United States Patent [19]

Monsma, Jr. et al.

[11] Patent Number: 5,914,236

[45] Date of Patent: Jun. 22, 1999

[54] PCT-65 SEROTONIN RECEPTOR

[75] Inventors: Frederick J. Monsma, Jr., Riehen, Switzerland; Yong Shen, Libertyville, Ill.; David R. Sibley, Gaithersburg, Md.; Mark Hamblin, Seattle, Wash.

[73] Assignee: United States of America, Washington, D.C.

[21] Appl. No.: 08/428,243

[22] PCT Filed: Oct. 26, 1993

[86] PCT No.: PCT/US93/10301

§ 371 Date: Sep. 18, 1995

§ 102(e) Date: Sep. 18, 1995

[87] PCT Pub. No.: WO94/10311

PCT Pub. Date: May 11, 1994

Related U.S. Application Data

[63] Continuation-in-part of application No. 07/980,514, Oct. 26, 1992, abandoned.

[51] Int. Cl.$^6$ .................. C12N 15/12; C07K 14/705; G01N 33/00

[52] U.S. Cl. .................. 435/7.21; 435/69.1; 435/320.1; 435/325; 435/369; 536/23.5; 530/350

[58] Field of Search .................. 435/6, 7.1, 7.2, 435/7.21, 69.1, 240.1, 252.3 T, 320.1, 325, 369; 536/23.5; 514/2, 12; 530/350

[56] References Cited

FOREIGN PATENT DOCUMENTS

WO 9117174  11/1991  WIPO .

OTHER PUBLICATIONS

Monsma, F J Jr., et al., "Cloning and Expression of a Novel Serotonin Receptor with High Affinity for Tricyclic Psychotropic Drugs," Molecular Pharmacology, 3(3):320–7, Mar. 1993.

Cheng, Y., et al., (1973) Relationship between the inhibition constant ($K_1$) and the concentration of inhibitor which causes 50 per cent inhibition . . . Biochemical Pharmacology 22:3099–3108.

Glennon, R. (1990) Serotonin receptors: clinical implications. Neuroscience & Biobehavioral Reviews 14:35–47.

Hamblin, M., et al., (1991) Primary structure and functional characterization of a human 5–HT$_{1D}$–Type serotonin receptor. Molecular Pharmacology 40:143–148.

Harlow, E., et al., Antibodies: A Laboratory Manual, Cold Spring Harbor Laboratory (1988).

Hen, R., et al. (1992) Of mice and flies: commonalities among 5–HT Receptors. Trends in Pharmacological Sciences 13:160–165.

Julius, D., et al., (1989) Ectopic expression of the serotonin 1c receptor and the triggering of malignant tranformation. Science 244:1057–1062.

Monsma, F., et al., Abstract 198.18, Oct. 25–30 1992; Society for Neuroscience Abstracts 18(1–2):465.

Monsma, F. , et al., Database WPI week 9319. Derwent Publications Ltd., London, GB; Abstract No. 93–159493 New Mammalian Serotonin Receptor Protein PCT–65 . . . (Apr. 01, 1993).

Murphy, D., (1990) Neuropsychiatric disorders and the muliple human brain serotonin receptor subtypes and subsystems. Neuropsychopharmacology 3(5,6):457–465.

Sambrook, J., et al., Molecular Cloning: A Laboratory Manual Second Edition, Cold Spring Harbor Laboratory Press (1989), pp. xi–xxxviii.

Shen, Y., et al., Abstract 467.2, Nov. 10–15, 1991; Society for Neuroscience Abstracts part 2:1173.

Shen, Y., et al., Abstract 198.17, Oct. 25–30 1992; Society for Neuroscience Abstracts 18(1–2):465.

Shen, Y., et al., (1993) Molecular cloning and expression of a 5–Hydroxytryptamine$_7$ . . . Journal of Biological Chemistry 268(24):18200–18204.

Takebe, Y., et al., (1988) SRα promoter: an efficient and versatile mammalian cDNA expression system composed of the simian virus 40 early promoter and the R–U5 segment of human T–cell . . . Molecular and Cellular Biology 8(1):466–472.

*Primary Examiner*—Marianne P. Allen
*Attorney, Agent, or Firm*—Knobbe, Martens Olson & Bear, LLP

[57] ABSTRACT

The PCT-65 serotonin receptor gene was cloned and characterized from rat and human libraries. This receptor has nucleotide and amino acid homology with previously described 5–HT genes and can bind ligands that are known to interact with serotonin receptors.

27 Claims, 4 Drawing Sheets

PCT-65 SEROTONIN RECEPTOR

This application claims priority from PCT Application No. PCT/US93/10301 filed on Oct. 26, 1993. This application is also a continuation-in-part of U.S. patent application Ser. No. 07/980,514, filed on Oct. 26, 1992, now abandoned.

FIELD OF THE INVENTION

This invention relates to cloning and characterization of cellular receptors. Specifically, this invention relates to the cloning and characterization of the PCT-65 serotonin receptor protein.

BACKGROUND OF THE INVENTION

The neurotransmitter serotonin (5-hydroxytryptamine, 5-HT) has a variety of functions in the central nervous system. It has been implicated in many cognitive and behavioral functions, including aggression, sexual behavior, learning and sleep. Disruptions of serotonergic systems may be a critical factor in a number of clinical disorders or conditions including schizophrenia, depression, obsessive compulsive disorder, anxiety, migraine headaches, and pain.

The multitude of effects produced by serotonin are mediated by various serotonin receptors which exist in the central and peripheral nervous system. The transduction of serotonergic signals across the neuronal membrane is believed to be mediated by a diversity of receptor subtypes which, in mammals, appear to fall into four pharmacologically distinct classes designated $5\text{-HT}_1$–$5\text{-HT}_4$. The $5\text{HT}_1$ subcategory has been further subdivided into five different subtypes referred to as $5\text{HT}_{1A\text{-}E}$. The primary structures for a number of these receptors have been elucidated by molecular cloning, including the $5\text{-HT}_1$, $5\text{-HT}_2$ and $5\text{HT}_3$ subclasses. In addition, the sequences of three different Drosophila serotonin receptors, $5\text{-HT}_{dro1}$ and $5\text{-HT}_{dro2A,B}$, have been reported.

Selective therapeutic agents, including agonist and antagonist drugs, have been developed based on serotonin receptor technologies utilizing the serotonin classes known in the art. $5\text{-HT}_2$ antagonists, for example, are useful in the treatment of schizophrenia, parkinsonism, and anxiety disorders. Several azapirones, such as buspirone, gepirone, and ipsapirone, have high affinities for $5\text{HT}_{1A}$ receptors in the brain, and are useful in the treatment of anxiety. Highly selective 5-HT uptake inhibitors, which have minimal effects on norepinephrine or dopamine uptake or on other neurotransmitter receptors, have been used to successfully treat depression.

Characterization of proteins with serotonin receptor activity would clarify the role of serotonin in the central nervous system. Analysis of the receptor proteins and their functional role in the central nervous system would help elucidate the pathophysiological basis of many human diseases. Accordingly, disclosed herein is a structurally and pharmacologically novel serotonin receptor which is distinct from any class of previously described 5-HT receptors.

BRIEF DESCRIPTION OF THE FIGURES

FIG. 3a-1 provides the results of binding studies to assess the ability of [$^3$H]-LSD to bind to the surface of COS-7 cells transfected with a PCT-65 containing construct. FIG. 3a-2 additionally includes a Scatchard analysis of the saturation data.

SUMMARY OF THE INVENTION

One embodiment of the present invention is the isolated mammalian serotonin receptor protein PCT-65. Preferably this receptor protein is human. The present invention also encompasses species variations of the PCT-65 receptor.

Another embodiment of the present invention is a method for screening a drug candidate for central nervous system activity by contacting the drug candidate with the PCT-65 protein and measuring binding of the drug candidate by the protein.

An additional embodiment of the present invention is a method for screening drug candidate for central nervous system activity by first contacting the PCT-65 serotonin receptor protein with a first molecule known to be bound by the protein to form a first complex of the protein and the first molecule; then contacting the first complex with the drug candidate; and finally measuring whether the drug candidate displaces the first molecule from the first complex. This method can preferably include in the measuring step, the step of measuring the formation of a second complex of the protein and the drug candidate. An alternative method of measuring the displacement of the first molecule can be accomplished by measuring the amount of the first molecule that is not bound to the protein.

A further embodiment of the present invention includes a recombinant construct of the polynucleotide, preferably the polynucleotide of SEQ ID NO: 6 encoding the PCT-65 serotonin receptor protein operably linked to a heterologous promoter.

Another embodiment of the present invention is directed at the polynucleotide sequence encoding the PCT-65 receptor. Preferably, this polynucleotide sequence is Sequence ID NO: 6 or species variations thereof. Additionally, the present invention encompasses an isolated nucleotide sequence having homology to at least 18 contiguous nucleotides of the PCT-65 gene.

The present invention also embodies a mammalian cell line, preferably human, in continuous culture expressing the PCT-65 serotonin receptor protein. Particularly, the cell line can contain the polynucleotide of Sequence ID NO: 6 or species variations thereof. One especially preferred embodiment includes HEK 293 immortalized cells in continuous culture expressing the PCT-65 receptor.

Yet another embodiment of the present invention is isolated antibodies against the PCT-65 serotonin receptor protein. Preferably these isolated antibodies are polyclonal; even more preferably, the isolated antibodies are monoclonal.

An even further embodiment of the present invention includes a method of screening a ligand for binding to the PCT-65 serotonin receptor by the steps of:
 transfecting a cell line with a gene encoding the PCT-65 serotonin receptor protein in an expression vector;
 culturing the cell line to express the gene in media containing a ligand of the receptor; and
 measuring the binding of the ligand the receptor produced by the cell line.
Preferably, in this method, the cell line is from a mammal, more preferably a human, and most preferably the cell line is HEK 293. An additional preferred embodiment of the above method entails transfecting cells with the PCT-65 serotonin receptor encoded by the polynucleotide of SEQ ID NO: 6. Additional preferred embodiments of this method include using eukaryotic expression vectors, preferably pSRα-65. Another preferred embodiment includes using ligands that are labeled with the label being either radioactive or colorimetric.

Still another embodiment of the present invention is a method of determining the ability of a drug to inhibit ligand binding to the PCT-65 serotonin receptor protein by the following steps:

transfecting a cell line with a DNA sequence encoding PCT-65 in an expression vector;

culturing the cell line to express the PCT-65 receptor in media containing a ligand of the receptor;

determining the level of binding of the ligand to the receptor;

culturing the same cell line to express the receptor in the presence of both the ligand and the drug; and determining the level of binding of the ligand to the expressed receptor, wherein a lower level of binding in the presence of the drug indicates that the compound is an inhibitor of ligand binding.

Preferably, the cell line of this method is mammalian, most preferably HEK 293, and the ligand, the drug or both are labeled. Additionally, the expression vector of this method can preferably be pSRα-65 and the ligand can advantageously be serotonin.

Still another embodiment of the present invention is a method of determining the ability of a drug to inhibit ligand binding to the PCT-65 serotonin receptor protein by the steps of:

transfecting a cell line with a DNA sequence encoding PCT-65 in an expression vector;

culturing the cell line to express the PCT-65 receptor in media containing a ligand of the receptor;

isolating the membranes from the cell line, wherein the membranes contain the expressed PCT-65 receptor;

determining the level of binding of the ligand to the receptor on the membranes;

incubating the membranes in the presence of both the ligand and the drug; and determining the level of binding of the ligand to the membranes, wherein a lower level of binding in the presence of the drug indicates that the compound is an inhibitor of ligand binding.

DETAILED DESCRIPTION OF THE INVENTION

This invention discloses the identification of a novel serotonin receptor, PCT-65, having both structure and pharmacological properties distinct from any class of previously described 5-HT receptors.

The gene sequence of PCT-65, vectors encoding this sequence, cells expressing PCT-65 from vectors encoding this sequence and substantially purified protein encoded by this sequence will be particularly useful for studying the cellular distribution of the protein. Additionally, assays using the expressed protein will be important tools for studying the pharmacological effects of serotonin receptor binding and blocking drugs. Knowledge of the PCT-65 gene sequence will also allow introduction of mutations into the protein to study protein function and receptor binding activity, and ultimately to the development and identification of agonists and antagonists with useful therapeutic potential.

This receptor appears to be localized predominantly in the hippocampus and hypothalamus of the central nervous system in addition to other limbic and cortical regions. Lower levels of this receptor are also found in the periphery including the spleen and kidney. When expressed in mammalian cells, this receptor exhibits high affinity for serotonin as well as a number of tricyclic antipsychotic and antidepressant drugs including clozapine, loxipine, and amitriptyline. The pharmacological properties that PCT-65 exhibits for these drugs, however, is different from any other known 5-HT gene. Thus, PCT-65 represents an unknown and uncharacterized receptor protein.

The present invention includes isolated PCT-65 serotonin receptors from rats, humans, other mammals, and other vertebrates. Further investigations of PCT-65's role in vivo and in vitro will help improve current therapies for several neuropsychiatric disorders by providing additional information on each drug's receptor mediated action.

While this gene sequence was originally isolated from rat kidney proximal convoluted tubule, and has been found to be expressed in various brain regions, it is anticipated that homologous proteins are similarly located in corresponding tissues from other vertebrates. Further, the methods disclosed herein can be used to identify protein from other vertebrates having similar pharmacologic properties. In addition, nucleotide and protein sequences of greater than or equal to 90% homology from other vertebrates can readily be located using the techniques of this invention.

IDENTIFICATION OF NOVEL MEMBERS OF THE G PROTEIN-COUPLED RECEPTOR FAMILY

As explained below in Example 1, degenerate polymerase chain reaction (PCR) primers SEQ ID NO: 1 and SEQ ID NO: 2 were synthesized by standard methods and modeled after sequences from the third and sixth transmembrane (TM) regions of previously cloned biogenic amine receptors.

The primers were used to amplify cDNA synthesized from poly (A)+ RNA purified from rat kidney proximal convoluted tubule cells. PCR amplification with the degenerate primers yielded a number of different cDNA fragments, some of which were determined by DNA sequence analysis to represent portions of previously cloned receptors. In addition, some putatively novel receptor DNA sequences, as well as unknown DNA sequences, were identified using this method. One putatively novel receptor cDNA fragment, termed PCT-65$_1$, exhibited high homology with previously cloned members of the serotonin receptor family and was selected for further study.

CHARACTERIZATION OF THE PCT-65 CLONE

Figure 1A:
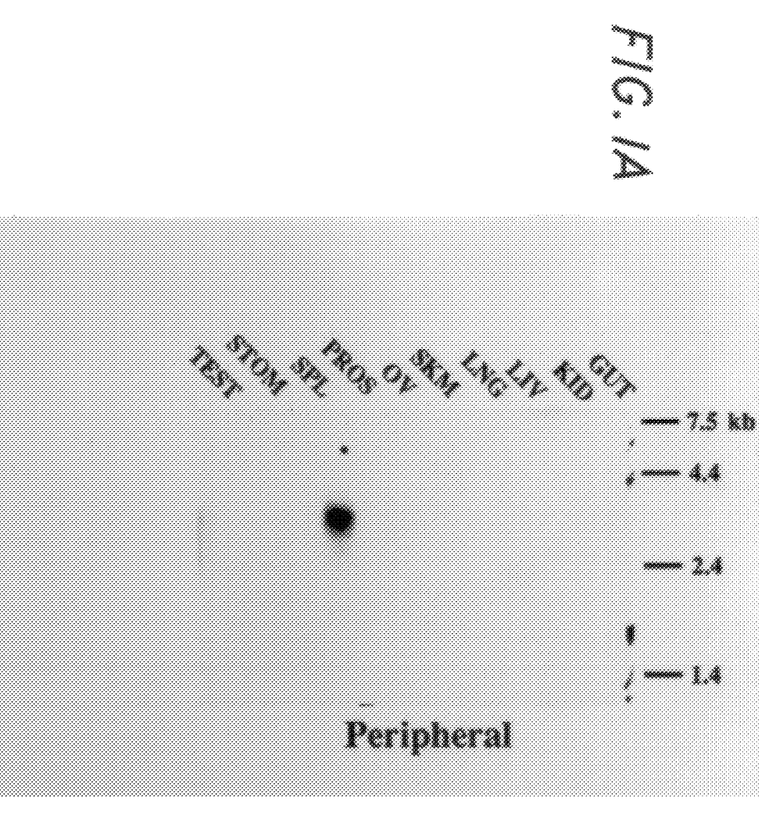
FIGS. 1A–B are photographs of Northern blots of rat Poly (A)+ RNA identifying PCT-65 mRNA from various central nervous system (CNS) and peripheral tissues. RNA size markers (in kilobases) is provided at the right of each blot.
Figure 1B:
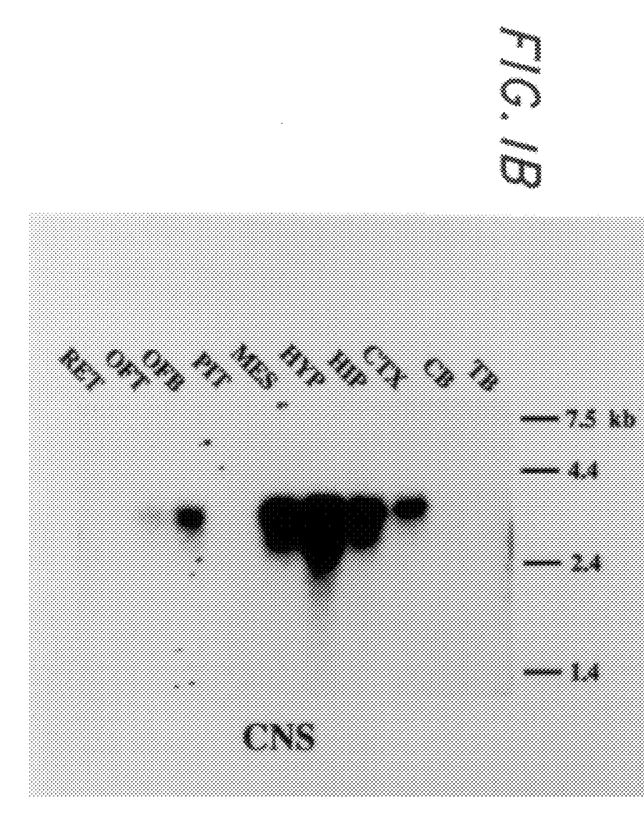

The tissue distribution of the corresponding mRNA was examined by Northern blot as an initial characterization of the PCT-65$_1$ clone, FIGS. 1A, 1B. To determine the tissue distribution of the clone, poly(A$^+$) RNA was prepared from a variety of vertebrate tissues. For example, rats were sacrificed and the tissue of interest was dissected from the animal. To preserve the integrity of the mRNA, the intact tissue sample was either flash frozen in liquid nitrogen or homogenized directly in guanidine isothiocyanate.

FIGS. 1A, 1B and photographs showing Northern blots of poly (A+) RNA prepared from a variety of rat tissues associated with the central nervous system as well as selected peripheral tissues. Techniques for obtaining poly (A$^+$) mRNA from tissue homogenates are well known in the art. Additionally, commercial kits are available for the preparation of poly (A$^+$) mRNA. Examples of commercially available kits are the FastTrack™ kits from Invitrogen (San Diego, Calif.) or those available from CINNA/BIOTECK, Laboratories International.

The Northern blots of FIG. 1 were probed with the isolated PCT-65$_1$ fragment (generated in Example 1) corresponding to transmembrane regions III and IV. The fragment was random primed using commercially available kits, such as those available from Stratagene, Inc. (San Diego, Calif.). The preferred methods for degenerate PCR construction and random priming are provided in Example 1.

Example 2 discloses a preferred Northern blotting procedure useful for identifying mRNA transcripts binding to the PCT-65$_1$ fragment. In this experiment, a single transcript of ~3.6 kb was observed in various homogenates from the central nervous system. The highest level of mRNA expression occurred in the hippocampus, however identifiable signals were present in the olfactory tubercle (OFT), mesencephalon (MES), hypothalamus (HYP), hippocampus (HIP) and cortex (CTX). The olfactory bulb (OFB) had reduced levels while the cerebellum (CB), the retina (REN) and the total brain homogenates (TB) had levels of mRNA that were very reduced.

In peripheral tissues, this mRNA transcript was identified most heavily in the spleen, whereas it was present in undetectable levels in the pituitary (PIT), testis (TEST), stomach (STOM), prostate (PROS), ovary (OV), skeletal muscle (SKM), lung (LNG), liver (LIV), kidney (KID) and gut (GUT). While kidney is the tissue of origin of the PCT-65 clone, the inability to detect PCT-65 mRNA in kidney via Northern blotting suggests that PCT-65 is either a minor transcript in the kidney or is restricted to a small population of cells.

ISOLATION OF A FULL LENGTH PCT-65 CLONE

Based on the high concentration of PCT-65 in the hippocampus by Northern blot analysis, we decided to screen a rat hippocampal cDNA library using the PCT-65$_1$ fragment in order to obtain a full-length clone. Library screening methods are well known in the art and preferred screening methods are disclosed in Example 3. One positive clone having a cDNA insert of ~2.9 kb was isolated. The complete nucleotide sequence was determined by the Sanger dideoxy nucleotide chain termination method using the commercially available Sequenase™ kit (US Biochemical Corporation).

The PCT-65 clone isolated from the rat hippocampal library screen was cleaved with EcoR1 to obtain a 1.5 kb fragment, PCT-65$_2$, (SEQ ID NO: 5) that was subcloned into pBluescript SKII (+) (Stratagene) following techniques provided by Stratagene. This EcoR1 fragment contained an open reading frame having sequences homologous to transmembrane regions I-VII of previously cloned serotonin receptors 5HT-1A, 5HT-1B, 5HT-1C, 5HT-1D, 5HT-1E and 5HT2. Careful inspection of the sequence further revealed the presence of putative intronic donor and acceptor sequences. This suggested the possibility that the rat hippocampal cDNA represented an incompletely-spliced RNA transcript.

The possibility that this intron was removed in the functional PCT-65 receptor protein was investigated by using PCR on a fresh preparation of rat hippocampal mRNA to amplify the putative intron region. Briefly, messenger RNA was purified from a fresh preparation of rat hippocampal tissue by standard, well known methods. The mRNA was converted into double stranded cDNA by reverse transcription using an oligo dT primer followed by second strand systhesis with DNA polymerase. PCR procedures on the cDNA were performed by the method disclosed in Example 1. Amplification across the intron region using primers P1 (SEQ ID NO: 3) and P2 (SEQ ID NO: 4) resulted in two cDNA products.

One cDNA corresponded to an unspliced RNA with a sequence similar to PCT65$_2$, whereas the other (PCT-65$_{2a}$) was an RNA molecule with the intron removed. Sequencing of the spliced cDNA (PCT-65$_{2a}$) confirmed our hypothesis that the putative intron was removed in the active PCT-65 receptor protein. The sequence of primer SEQ ID NO: 4 (below) is complementary to the coding sequence since it was designed to hybridize with the opposite nucleotide strand.

P1 5'-GATCTTCGGC CACTTCTTCT GCAACGTCTT-3' (SEQ ID NO: 3)
P2 5'-TGGGAACTTG TGTTTGGCTG CACTCTTCCT-3' (SEQ ID NO: 4)

This result suggested that there were two forms of RNA in the hippocampus with only one of the RNA forms being completely spliced. A properly spliced version of the PCT-65 receptor is shown in SEQ ID NO: 6 and the corresponding protein is shown in SEQ ID NO: 7.

We compared the homologous regions between PCT-65 and the Drosophila 5HT receptor (Dro-1), 5HT$_{1A}$, 5HT$_{1B}$, 5HT$_{1C}$, 5HT$_{1D}$, 5HT$_{1E}$, 5HT$_2$, the 5HT-receptor like (SRL) from stomach fundus tissue, and a novel 5HT receptor from rat striatum (STB-17). Within the transmembrane regions, the PCT-65 receptor is between 37%–56% homologous to previously cloned 5HT receptors. The homologies indicated that although the PCT-65 receptor has significant sequence similarities to the previously cloned serotonin receptor subtypes, sequence differences are plainly evident.

EXPRESSION OF PCT-65 ENCODING PROTEIN IN MAMMALIAN CELLS

To provide the assays necessary for studying the pharmacological binding pattern of drugs which affect serotonin receptors, PCT-65 was expressed in eukaryotic cells. There are a variety of expression vectors and cell types available in the art to facilitate protein expression. In the embodiment disclosed in Example 3, PCT-65 was inserted into the pSRα mammalian expression plasmid (Takabe et al., (1988) *Molec. Cell Biol.* 8: 466–472) and transfected into mammalian COS-7 cells.

Figure 2:
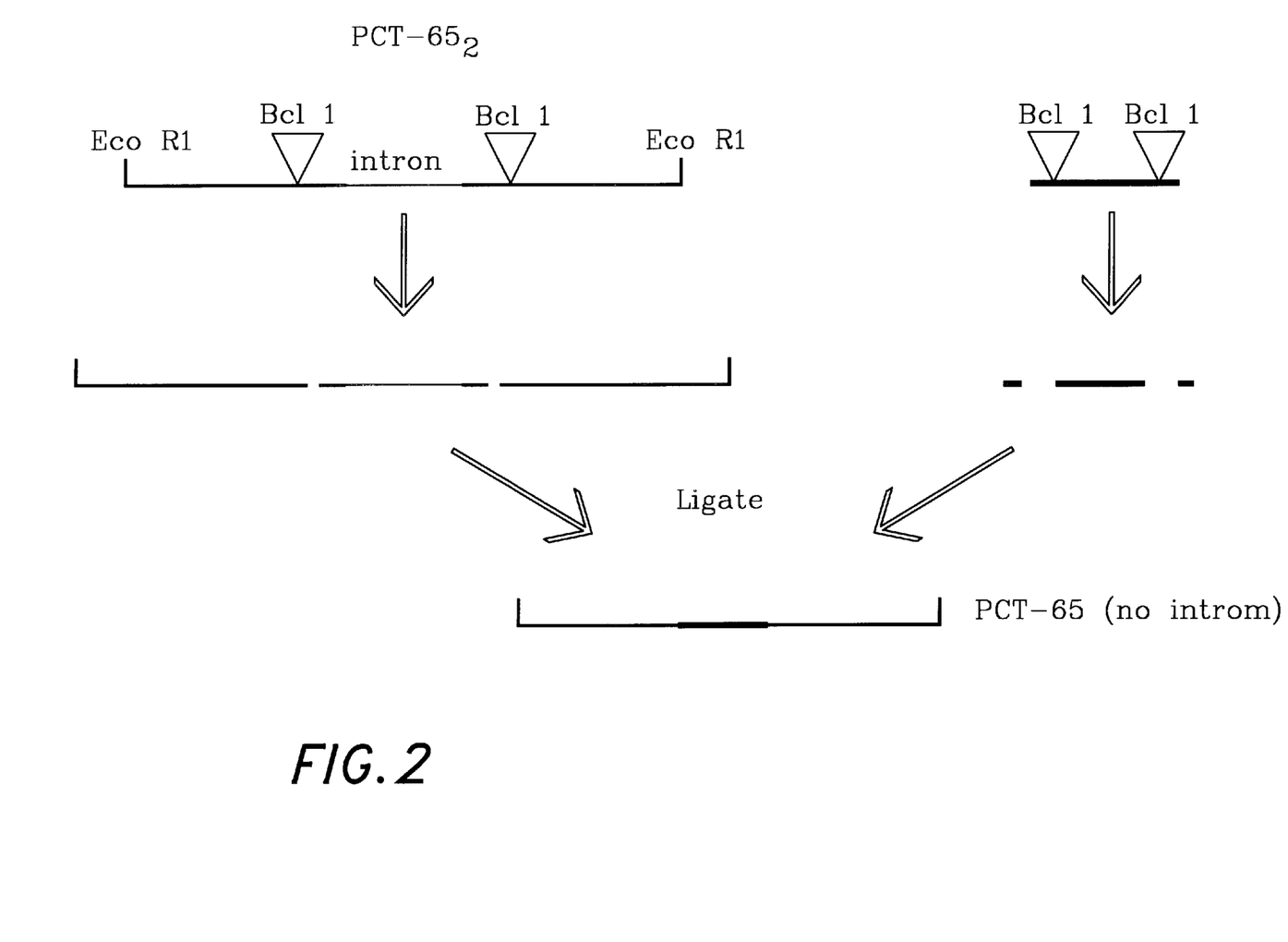
FIG. 2 illustrates the cloning procedure used to derive the PCT-65 clone without an intron for expression studies.

To properly express the PCT-65 receptor, the PCT-65$_2$ fragment was modified to remove the intron sequence by the procedure outlined in FIG. 2. Briefly, the PCT-65$_2$ fragment, containing the entire gene sequence and intron was digested with Bcl 1 (Boehringer Mannheim, Indianapolis, Ind.). The PCT-65$_{2a}$ fragment (having a properly spliced region between the Bcl 1 sites) was digested and ligated back together with the Bcl 1 fragments from PCT-65$_2$. The reconstructed PCT-65 receptor gene (with the full coding sequence and no intron) was subcloned into pSRα at the EcoR1 site.

The resulting construct (pSRα-65) was transfected by calcium phosphate-mediated transfection into Cos-7 cells (American Type Culture Collection, Rockville Md.) using the methods described in Sambrook et al. (*Molecular Cloning: A Laboratory Manual* (1990) Cold Spring Harbor, N.Y.).

ASSAYS TO DETERMINE PCT-65 SEROTONIN RECEPTOR INHIBITORY DRUGS

The molecular cloning and expression of the PCT-65 serotonin receptor will be useful in the development of drugs which interact at this binding site. For instance, the cloning of the PCT-65 receptor protein provided new assays for discovering serotonin receptor binding and inhibitory drugs. These assays were performed by transfecting Cos-7 cells, as discussed above, and placing them in media to express the PCT-65 receptor on their cell surface (Example 4). The cells were lysed and the membranes isolated for binding studies.

Radiolabeled ligands were then tested for binding to the isolated membranes from these cells.

Figure 3A:
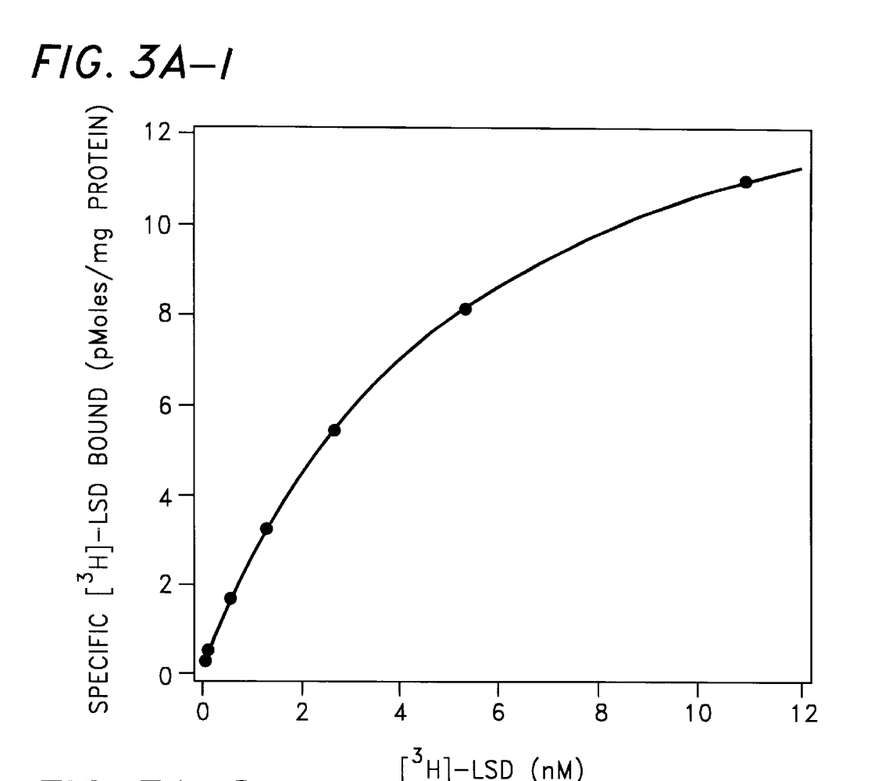
Figure 3A:
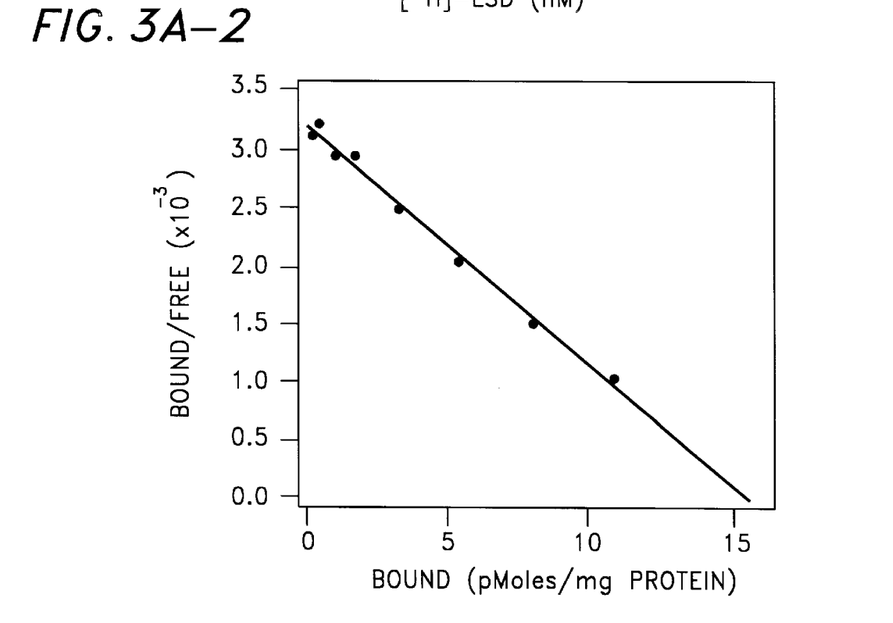

By using this method we were able to screen many drugs for their binding activity to the serotonin receptor. Similarly, this assay system was used to detect competitive inhibitors of serotonin binding. Incubation of the PCT-65 transfected cells in the presence of [$^3$H]-LSD, a known 5-HT binding molecule, led to our determination of LSD's binding and saturation point for the PCT-65 receptor. These experiments are discussed in Example 4 and illustrated in FIG. 3a-1. Approximate [$^3$H]-LSD concentrations o9f 10 nM to 12 nM are shown to saturate the PCT-65 receptor. The standard saturation curve underscores our contention that PCT-65 is a serotonin receptor protein.

Since serotonin binding is intimately involved in the functionality of the central nervous system, assays for detecting drugs which bind or block serotonin receptors are of paramount importance. As discussed in the background, many behavioral functions are believed to be mediated through serotonergic systems. For researchers to accurately assess the effects of a new serotonin related drug in humans, it is important to test that drug's effect on every known serotonin receptor. The discovery of the PCT-65 serotonin receptor provides the researcher with a previously unknown assay to study possible in vivo effects of future central nervous system drugs.

This discovery thereby leads to methods of screening drug candidates for central nervous system activity by testing their binding to isolated PCT-65. We believe that drugs which bind to the PCT-65 receptor in vitro will also have effects in vivo. In addition to directly measuring the binding of a drug to the PCT-65 receptor, we were also able to measure the displacement of known binding ligands to the PCT-65 receptor. By measuring the binding of a ligand as discussed above, and then comparing that binding to the level of affinity in the presence of a drug candidate, we were able to estimate the potential of the drug to displace the ligand (Example 5).

We also anticipate that the isolated PCT-65 receptor protein will be useful for performing assays to determine agents which inhibit binding to serotonin receptors. In discussing the isolated PCT-65 receptor, we include not only purified protein Example 9, but cell membranes containing expressed PCT-65 isolated from the cell. For example, we transfected Cos-7 cells with the gene encoding the PCT-65 receptor protein in an expression plasmid. After incubation in media to allow PCT-65 receptor expression, the cells were lysed and the membranes (containing the bound PCT-65 receptors) were pelleted. These membranes, isolated from the host cells, were used for radiolabeled ligand binding studies (Example 5).

Figure 3B:
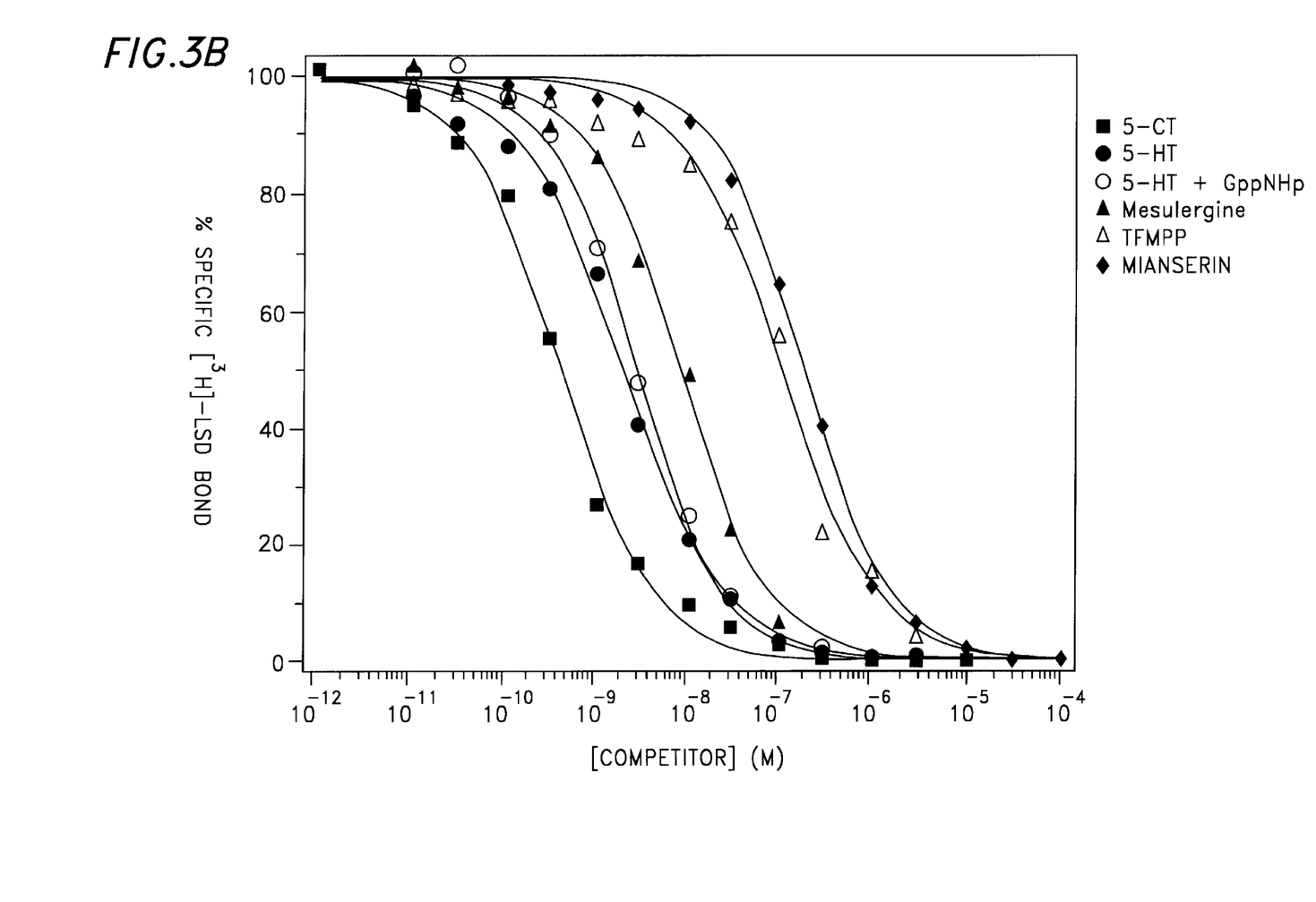
FIG. 3b illustrates the pharmacological specificity of [$^3$H]-LSD binding to transfected COS-7 cells in the presence of various serotonin agonists and antagonists as well as the effect of PCT-65 receptor modulation using Gpp(NH)p.

Assays provided by the present invention involve the utilization of a variety of drugs which are known to exhibit specificity for various serotonergic receptor subtypes and other binding sites. The average constant of inhibition ($K_i$) values for compounds competing with better than 10 $\mu$M affinity are shown in Table 1 with representative competition curves for [$^3$H]-LSD binding shown in FIG. 3b.

Examination of the rank order of potency for a variety of serotonergic agents reveals that the pharmacology of the PCT-65 receptor does not correspond to any previously described serotonin receptor subtype. A number of drugs selective for other 5-HT receptor subtypes such as 8-OH-DPAT (5HT$_{1A}$) bind with relatively low affinity. Ergot alkaloids, especially ergoline derivatives (i.e., LSD, lisuride, or pergolide) and mesulergine (5-HT$_{1C}$) display relatively high affinity for PCT-65 as does the non-selective serotonergic antagonist methiothepin.

Interestingly, the typical anti-psychotic loxapine exhibited low affinity for PCT-65, while the atypical psychotic drug clozapine had high affinity for PCT-65. One tricyclic anti-depressant drug (amitriptyline) had a $K_i$ value under 100 nM. In general, the drugs which exhibited the greatest affinity for PCT-65 (i.e., $K_i$<100 nM) were tricyclic, ergoline or tryptamine derivatives.

Competition for [$^3$H]-5-HT (serotonin) binding by a number of drugs revealed, with a few exceptions, the same rank order of potency as for inhibition of [$^3$H]-LSD binding (Table 1). However, the $K_i$ values for some drugs were determined by competition with [$^3$H]-5-HT and found to be up to 5-fold lower than those determined by competition with [$^3$H]-LSD, with the exception of metergoline and clozapine which exhibited somewhat greater potency in competition with [$^3$H]-LSD.

These competition assays provide methods of screening potential central nervous system drugs for their potential pharmacological effects in vivo. It is also anticipated that the PCT-65 receptor screening assays will be very important for determining the potential dosages of putative drugs prior to introduction in vivo.

Other assay methods are also anticipated by the present invention. For example, the expression of PCT-65 on the cell surface can be detected by either polyclonal or monoclonal antibodies directed against PCT-65 epitopes. Possible disease states wherein a defective PCT-65 receptor is expressed could thus be detected by comparison of antibody binding of normal cells to binding of the disease state cells. Methods of producing antibodies against PCT-65 are discussed in Examples 7 and 8.

Additionally, the PCT-65 serotonin receptor can be purified by antibody affinity chromatography (Harlow et al. *Antibodies—A Laboratory Manual,* Cold Spring Harbor (1988) N.Y.). In one embodiment of this method, monoclonal antibodies produced in Example 9 are attached to an affinity column, and contacted with transfected Cos-7 cell lysates. The bound proteins are eluted off in a low pH solution by standard methods.

In situ hybridization methods Example 9 can be used to determine mRNA expression in rat hippocampal tissue. Briefly, rat brains are isolated and incubated in a hybridization solution comprising radiolabeled primer P1. The labeled primer enters the sectioned brain sample and hybridizes with the cytoplasmic mRNA resulting in a detectable signal on an autoradiograph. It is also contemplated that other methods of labeling the PCT-65 specific oligonucleotide are within the scope of this invention. Other methods of labeling could be colorimetric or enzymatic.

Particular embodiments of the invention will be discussed in detail and reference will be made to possible variations within the scope of the invention. There are a variety of alternative techniques and procedures available to those of skill in the art which would similarly permit one to obtain the elements of this invention.

EXAMPLE 1

Identification of the PCT-65 Clone

Total RNA was prepared from rat kidney proximal convoluted tubule (PCT) using RNazol B (CINNA/BIOTECK, Laboratories International) and poly A+ RNA was isolated using poly-A Quick columns (Stratagene). First strand cDNA synthesized from the rat PCT mRNA was amplified by PCR with 1 $\mu$M each of the following primers:

5' GTCGACCCT(GT)T(GT) (CG)GCC(AC)TCA(GT) CA(TC) (GA)G(AG)TCGCTA-3'SEQ ID NO: 1

5'-AAGCTTATGAA(AG)AAGGGCAG(GC)CA(AG)
CAGAGG(TG) (CT) (AG)(CA)A-3'SEQ ID NO: 2

The PCR reaction proceeded for 1.5 min at 93° C., 2 min at 50° C., and 4 min at 72° C. followed by a 7 min extension at 72° C. The reaction products were purified by ultrafiltration with Centricon 30 units (Amicon), digested with Sal I and Hind III, and gel isolated on a 1% agarose gel. Individual bands were excised, electroeluted, concentrated by ultrafiltration, and ligated into Sal/Hind III digested pBluescript II SK (+) (Stratagene).

Competent DH5α cells (Invitrogen) were transformed and minipreparations of the plasmid DNA was prepared for insert sequencing using the Sanger dideoxy nucleotide chain termination method with Sequenase (US Biochemical Corp.) One clone PCT-65$_1$ having homology to other serotonin receptors was chosen for further study.

EXAMPLE 2

Tissue Distribution of PCT-65 by Northern Blot Analysis

Poly (A)$^+$ RNA was isolated from rat brain and peripheral tissues. Samples (1 μg in each lane) were denatured and electrophoresed through 1% agarose gel having 0.66 M formaldehyde, then transferred to nylon membrane (GeneScreen Plus, DuPont) by capillary transfer and immobilized by UV cross-linking. Northern blots were probed with PCT-65$_1$ PCR product amplified from the region between TM III and TM VI and $^{32}$P-labelled by the random primer method. The hybridization was carried out using 1×10$^6$ dpm/ml of the probe in 1 M NaCl, 1% SDS, 50% formamide, 10% Dextran Sulfate at 60° C. for 18 hr. Blots were washed in 2X SSC at room temperature, followed by 2X SSC with 1% SDS at 65° C., and then exposed for 15 days at −70° C. to X-ray film with an intensifying screen.

EXAMPLE 3

Identification of a Full Length PCT-65 Clone

1×10$^6$ recombinants from a rat hippocampal cDNA library, constructed in the λ gt 11 vector (Stratagene), were screened with a PCR fragment PCT-65$_1$ which was $^{32}$P-labeled via nick translation. Duplicate nitrocellulose filters were hybridized in 50% formamide, 0.75 M NaCl/0.075 M sodium citrate (5X SSC), 5X Denhardt's solution, 0.1% Na$_2$HPO$_4$, 01.% SDS, 0.15 mg/ml salmon sperm DNA, and 1.5×10$^8$ dpm/ml of $^{32}$P-labeled probe for 36 hr at 42° C.

The filters were washed at high stringency conditions: 2X SSC and 0.1% SDS at room temperature for 30 min and with 0.2X SSC and 1% SDS at 68° C. for 1 hour prior autoradiography. λ phage found to hybridize to the probe were subsequently plaque purified. One positive clone contained a 2.9 kb insert, from which a 1.5 kb fragment was removed with EcoR1 and subcloned into pBluescript SK II(+) by standard methods. The 1.5 kb EcoR1 fragment (PCT-65$_2$; SEQ ID NO: 5) was nucleotide sequenced using the Sanger dideoxy method.

As discussed above, a 73 nucleotide intron was discovered beginning at nucleotide +415 of PCT-65$_2$. Example 4 below shows the method we used to analyze the expression and binding properties of PCT-65.

EXAMPLE 4

Ligand Binding Assays Using the PCT-65 Receptor

We removed the intron of clone PCT-65$_2$ by digesting with Bcl 1. This cloning procedure is illustrated in FIG. 2. Briefly, we digested the spliced version (ie: without intron) of the PCT-65 cDNA (PCT-65$_{2a}$) with Bcl 1 and mixed these fragments and those derived from the Bcl 1 digestion of PCT-65$_2$. The fragment pool was incubated and ligated by well known methods. Fragments having EcoR1 sites were ligated into pBluescript and nucleotide sequenced.

One clone (PCT-65) having the entire coding sequence, but missing the intron, was subcloned into the expression vector pSRα. This plasmid construct (pSRα-65) was introduced into COS-7 cells by calcium phosphate-mediated transfection. Cells were harvested 3 days after transfection in 5 mM Tris-HCl, pH 7.4 at 37° C., 5 mM MgCl$_2$, 250 mM sucrose, and stored in liquid N$_2$ prior to membrane preparation.

Crude membranes were prepared from cell homogenates by centrifugation at 43,000×g for 10 min and the resulting pellets resuspended in the binding buffer: 50 mM Tris-HCl, 1.5 mM CaCl$_2$, 4.0 mM MgCl$_2$, 5.0 mM KCl, 120 mM NaCl and 1.0 mM EDTA, pH7.4, 25° C., at a protein concentration of 25–35 μg/ml.

For saturation experiments (FIG. 3a), 0.1 ml of the membrane suspension was incubated in a final volume of 1 ml with increasing concentrations of [$^3$H]-LSD (67 Ci/mMole, 78–10,000 pM), 200 μM sodium metabisulfate in triplicate for 60 min at 37° C. 100 μM of 5-HT was utilized to determine non-specific binding. FIG. 3a-1 illustrates the saturation binding of [$^3$H]-LSD to the PCT-65 receptor.

EXAMPLE 5

Pharmacological Competition Studies Using the PCT-65 Serotonin Receptor

Table 1 (below) shows varying concentrations of of the indicated competing ligands ($10^{-11}$ M–$10^{-5}$ M) which were utilized to study the binding inhibition of [$^3$H]-LSD (1.5–2.2 nM) or [$^3$H]-5-HT (1 nM) to membranes prepared from the COS-7 cells transiently transfected with clone PCT-65 as explained in Example 4.

Inhibition constant (Ki) values (Table 1) were obtained by correction of graphically determined IC$_{50}$ values according the method of Cheng and Prussof (Biochem. Pharmacol. 22, 3099–3108 (1973)) and are presented as the geometric mean±SEM (n=3)

Competition assays were initiated by addition of 0.1 ml of the membrane suspension and incubated in triplicate with about 2 nM [$^3$H]-LSD or about 1 nM [$^3$H]-5-HT, 200 μM sodium metabisulfite, and increasing concentrations of competing ligands ($10^{-11}$ to $10^{31\ 5}$ M) at 37° C. for 60 min.

The assays were terminated by rapid filtration through Whatman GF/C filters pretreated with 0.3% polyethyleneimine and washed four times with 3 ml of 50 mM Tris-HC1, pH7.4, at 4° C. Radioactivity levels were determined by liquid scintillation counting at an efficiency of 47%. Competition experiments for the [$^3$H]-5HT were performed in triplicate as described by Hamblin et al. (Molec. Pharm. (1991) 40: 143–148).

Specifically, transfected cells were scraped into PBS with 5 mM EDTA, spun, polytroned, spun, suspended in 100 mM Tris, 20 mM MgSO4, 1 mM EDTA, pH7.7. 0.5 ml of this solution containing 10–25 μg protein was added to 0.5 ml of a 2 mM ascorbic acid solution containing the ligand and drugs and incubated for 30 min at 37° C. Filtration was performed on GF/C paper (0.1% PEI solution pre-treatment) with a 10 ml rinse.

The following compounds which are not in Table 1 were tested and found to have Ki values >1.3 mM: Imipramine, NAN-190, Desipramine, Citalopram, Fluoxetine, Idazoxan, Quipazine, LY-278584, Octopamine, MDL7222, BRL24294, BRL43694, BIMU1, BIMU8, DAU6215, DAU6285, GR38032, Zacopride, Fenflurmine, Pindolol, Dopamine, Norepinephrine, Histamine, and Melotonin.

TABLE 1

Ki (nM) values for [3H]-LSD and [3-H]-5HT binding to the PCT-65 receptor expressed in COS-7 cells

| Drugs | Ki (nM) ± SEM | |
|---|---|---|
| | vs. [$^3$H]-LSD | vs. [$^3$H]-5-HT |
| 5-Carboxamidotryptamine | 0.33 ± 0.01 | 0.16 ± 0.05 |
| Lisuride | 0.52 ± 0.12 | 0.89 ± 0.32 |
| Methiothepin | 1.03 ± 0.16 | 0.38 ± 0.18 |
| 5-Methoxytryptamine | 1.78 ± 0.05 | 0.57 ± 0.03 |
| 5-Hydroxytryptamine | 1.83 ± 0.07 | 1.52 ± 0.27 |
| Metergoline | 2.04 ± 0.15 | 6.21 ± 1.00 |
| Pergolide | 4.78 ± 0.18 | 1.01 ± 0.03 |
| Mesulergine | 7.13 ± 0.39 | 21.1 ± 2.19 |
| Bromocriptine | 10.72 ± 0.47 | 48.80 ± 7.90 |
| Methysergide | 12.55 ± 0.84 | 13.40 ± 0.80 |
| Clozapine | 13.55 ± 2.61 | 39.50 ± 9.60 |
| 5-Methoxy-N, N-dimethytryptamine | 20.93 ± 0.86 | 8.26 ± 0.73 |
| Ritanserin | 21.71 ± 2.10 | 15.00 ± 3.40 |
| Tryptamine | 32.85 ± 0.76 | 16.42 ± 1.01 |
| 1(1-Napthyl)piperazine | 33.75 ± 1.68 | 18.39 ± 0.77 |
| 8-OH-DPAT | 35.44 ± 5.24 | 35.00 ± 5.62 |
| Cyproheptidine | 48.01 ± 3.26 | 34.10 ± 4.15 |
| Mianserin | 111.60 ± 13.84 | 36.90 ± 2.60 |
| Amitriptyline | 123.97 ± 13.37 | 92.80 ± 15.80 |
| Loxapine | 171.53 ± 7.80 | 133.00 ± 36.10 |
| Ketanserin | 206.79 ± 19.56 | 265.00 ± 32.10 |
| 2-MPP | 243.59 ± 16.47 | 125.00 ± 8.40 |
| mCPP | 352.05 ± 54.91 | 256.00 ± 9.90 |
| TFMPP | 532.93 ± 33.04 | 236.00 ± 5.50 |
| Sumatriptan | | 251.00 ± 36.10 |

Since Cos-7 cells are only transiently transfected, we stably transfected Human Embryonic Kidney cells (HEK 293 available from the ATCC) in 150 mm dishes by the CaPO$_4$ technique with 30 μg of PCT-65 (SEQ ID NO: 6) and 3 μg of pMam-neo (INVITROGEN). These HEK 293 cells were then subjected to selection with 600 μg/ml genetecin (G418) (GIBCO). The resistant colonies were collected and screened for receptor expression by [$^3$H]-LSD binding as described in Example 4. Assays using transfected HEK-293 cells revealed similar saturation and drug inhibitory patterns as that found with transfected Cos-7 cells.

We were also interested in isolating the human variation of the PCT-65 gene sequence. Our method of isolating the human receptor can be found in the following example.

EXAMPLE 6

Isolation of the Human Receptor

A 1349 bp NotI-EcoRI restriction fragment derived from the rat 5-HT$_7$ receptor cDNA pct65 was labeled with [α$^{32}$P]-dCTP using the nick-translation method and used to screen a commercially available human hypothalamic cDNA library (Clontech #29068) constructed in the viral vector λGT10. The library was plated using the host cell C600, followed by duplicate nylon (Nytran, Schleicher and Schuell) lifts.

Probe hybridization (6 X SSC at 55° C., pH7) and washing (2 X SSC, 58° C.) were then performed by well known methods at moderate stringency. Positive isolates were plaque purified through a second round of hybridization. In the second round, cDNA inserts from purified isolates were excised with EcoRI and then subcloned into the corresponding site in the phagemid vector pBluescript SK(−) (Stratagene). The nucleic acid sequence of these inserts were then determined by dideoxynucleotide termination using Sequenase (United States Biochemicals) in conjunction with standard subcloning techniques. This method allowed the sequencing of vitually the entire gene. Only about 117 nucleotides of the 5' end are missing. The nucloetide sequence of the majority of human PCT-65 receptor is SEQUENCE ID NO: 8 which encodes the protein of SEQUENCE ID NO: 9. One of ordinary skill in the art could use these same methods to determine the remaining nucleotide sequences of the 5' end.

It should be recognized that all of the previous experiments relating to identification of binding ligands to the rat receptor can be performed in a similar fashion with the human gene. For instance, the human gene can be cloned into an expression plasmid and placed in COS-7 cells by methods similar to those discussed above, and used to assay binding of competitors such as those revealed in Table 1. This would provide a method of assaying inhibitors of serotonin binding to the PCT-65 receptor.

Other experiments are also contemplated relating to discovering which cells in vivo express the receptor gene on their surface. One method of studying the expression of the PCT-65 receptor on cell surfaces throughout the body, is to produce antibodies against the receptor protein. A method for producing polyclonal antibodies is discussed below in Example 7.

EXAMPLE 7

Production of Antibodies Against PCT-65

COS-7 cells expressing the PCT-65 receptor protein derived in Example 4 are lysed with NP40, and the isolated membranes are injected into rabbits. The lysed membranes are isolated in a non-ionic detergent so as not to affect the membrane bound receptors. Freunds adjuvant is used in the injection to help stimulate an antigenic response by the rabbits. After two booster shots of the lysed membranes, the rabbits are bled and the sera isolated by centrifugation.

The antibodies in the crude rabbit sera extract are $^{125}$I labeled by well known methods, and tested for activity against the transfected COS-7 cells. A western blot having one lane containing proteins from transfected cell lysates, and a second lane having untransfected lysates (control) is run. A strong band indicating antibody binding in the transfected cell lane, that is not apparent in the untransfected lane demonstrates that polyclonal antibodies against the PCT-65 receptor protein have been properly isolated.

Monoclonal antibodies can be produced by well known methods in addition to the polyclonal antibodies discussed above. One method of producing monoclonal antibodies is discussed below in Example 8.

EXAMPLE 8

Production of Monoclonal Antibodies Against PCT-65

The PCT-65 transfected COS-7 cells produced in the previous examples are lysed with NP-40 and the cell membranes are pelleted by centrifugation. The isolated membranes, having bound PCT-65 receptor proteins, are co-injected with Freunds adjuvant into mice. After being re-injected 9 times over a three week period, the murine spleens are removed and resuspended in PBS.

The suspended spleen cells are mixed (approximately 4:1) with SP 2/0 Myeloma cells. Polyethylene glycol is added to fuse the myeloma cells to the spleen cells, and the fused cells are selected in HAT media. The fused cells are aliquoted so that only one cell is grown in each well of a 96 well microtiter plate. Each cell is grown, the media removed, and secreted proteins are $^{125}$I labeled. The labeled media from each well is used to probe a Western blot of transfected and untransfected COS-7 cell lysates (see Example 4).

The desired fusion cell produces a monoclonal antibody that strongly binds a band in the transfected COS-7 cell lane on the Western blot, but doesn't bind to any other protein in that lane, or the control lane. This method thereby discloses a procedure for detecting those cells expressing the PCT-65 serotonin receptor.

Another method of detecting the expression of PCT-65 is through in situ hybridization as discussed below in Example 9.

EXAMPLE 9

In situ Hybridization of PCT-65

In situ hybridization allows the identification of mRNA within intact tissues, such as the rat hippocampus. In this method, oligonucleotides corresponding to unique portions of the PCT-65 gene (SEQ ID NO: 6) are used to detect specific mRNA species in the hippocampus.

An anesthetized rat is transcardially perfused with cold PBS (5–20 minutes), followed by perfusion with a 4% formaldehyde solution. The brain is removed, frozen in liquid nitrogen, and cut into 5 μm to 30 μm sections. The sections are placed on slides and incubated in proteinase K for approximately 15 minutes. The slides are then rinsed in DEP, water, ethanol, and placed in a prehybridization buffer.

A radioactive probe corresponding to primer P1 is produced by nick translation and incubated with the sectioned hippocampal tissue. After incubation and air drying the labeled areas are visualized by autoradiography. Dark spots on the autoradiograph corresponding to the tissue sample indicate hybridization of the probe with the hippocampal mRNA thereby demonstrating expression of the PCT-65 receptor.

While particular embodiments of the invention have been described in detail, it will be apparent to those skilled in the art that these embodiments are exemplary, rather than limiting, and the true scope of the invention is that defined in the following claims.

---

We claim:

1. Isolated mammalian serotonin receptor protein PCT-65, said protein being localized predominantly in the hippocampus, hypothalamus and spleen of a mammal, and exhibiting high affinity binding to serotonin and clozapine.

2. The receptor protein of claim 1, wherein said protein is human PCT-65.

3. A recombinant construct comprising a polynucleotide encoding the mammalian serotonin receptor of claim 1 operably linked to a heterologous promoter.

4. The recombinant construct of claim 3, wherein said polynucleotide is SEQ ID NO: 6.

5. An eukaryotic cell line in continuous culture expressing the PCT-65 serotonin receptor protein of claim 1.

6. The mammalian cell line of claim 5, wherein said PCT-65 serotonin receptor protein is encoded by SEQ ID NO: 6.

7. The cell line of claim 5, wherein said cells are derived from a human.

8. The cell line of claim 5, wherein said cells are HEK 293.

9. A method of screening a ligand for binding to the PCT-65 serotonin receptor protein of claim 1, said method comprising the steps of:

transfecting a eukaryotic cell line with a gene encoding said PCT-65 serotonin receptor protein in an expression vector;

culturing said eukaryotic cell line to express said gene in media containing a ligand of said receptor; and measuring the binding of said ligand to said receptor produced by said eukaryotic cell line.

10. The method of claim 9, wherein said eukaryotic cell line is from a mammal.

11. The method of claim 9, wherein said PCT-65 serotonin receptor is encoded by the polynucleotide of SEQ ID NO: 6 or SEQ ID NO: 8.

12. The method of claim 9, wherein said eukaryotic cell line is HEK 293.

13. The method of claim 9, wherein said expression vector is pSRα-65.

14. The method of claim 9, wherein said ligand is labeled.

15. The method of claim 14, wherein said label is radioactive.

16. The method of claim 14, wherein said label is colorimetric.

17. A method of determining the ability of a drug to inhibit ligand binding to the PCT-65 serotonin receptor protein of claim 1, the method comprising:

transfecting a eukaryotic cell line with a DNA sequence encoding said PCT-65 serotonin receptor in an expression vector;

culturing said eukaryotic cell line to express said PCT-65 receptor in media containing a ligand of said receptor;

determining the level of binding of said ligand to said receptor;

culturing the same eukaryotic cell line to express said receptor in the presence of both said ligand and said drug; and determining the level of binding of said ligand to said expressed receptor, wherein a lower level of binding in the presence of said drug indicates that said drug is an inhibitor of ligand binding.

18. The method of claim 17, wherein said cell line is mammalian.

19. The method of claim 17, wherein said ligand is labeled.

20. The method of claim 17, wherein said drug is labeled.

21. The method of claim 17, wherein said cells are HEK 293.

22. The method of claim 17, wherein said expression vector is PSRα-65.

23. The method of claim 17, wherein said ligand is serotonin.

24. A method of determining the ability of a drug to inhibit ligand binding to the PCT-65 serotonin receptor protein of claim 1, the method comprising:

transfecting a eukaryotic cell line with a DNA sequence encoding said PCT-65 serotonin receptor in an expression vector;

culturing said eukaryotic cell line to express said PCT-65 receptor in media containing a ligand of said receptor;

isolating the membranes from said eukaryotic cell line, wherein the membranes contain the expressed PCT-65 receptor;

determining the level of binding of said ligand to said receptor or said membranes;

incubating said membranes in the presence of both said ligand and said drug; and determining the level of binding of said ligand to said membranes, wherein a lower level of binding in the presence of said drug indicates that said drug is an inhibitor of ligand binding.

25. The receptor protein of claim 1, wherein said protein is rat PCT-65.

26. The receptor protein of claim 25, wherein said rat PCT-65 is SEQ ID NO: 7.

27. An isolated polynucleotide comprising the DNA sequence of SEQ ID NO: 6 or SEQ ID NO: 8.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 33 base pairs
      (B) TYPE: nucleic acid
      (C) STRANDEDNESS: single
      (D) TOPOLOGY: linear    (ii) MOLECULE TYPE: cDNA to mRNA    (iii) HYPOTHETICAL: NO    (iv) ANTI-SENSE: NO    (xi) SEQUENCE DESCRIPTION: SEQ ID NO:1:

GTCGACCCTK TKSGCCMTCA KCAYRGRTCG CTA      33

(2) INFORMATION FOR SEQ ID NO:2:

(i) SEQUENCE CHARACTERISTICS:
      (A) LENGTH: 35 base pairs
      (B) TYPE: nucleic acid
      (C) STRANDEDNESS: single
      (D) TOPOLOGY: linear    (ii) MOLECULE TYPE: cDNA to mRNA    (iii) HYPOTHETICAL: NO    (iv) ANTI-SENSE: YES    (xi) SEQUENCE DESCRIPTION: SEQ ID NO:2:

AAGCTTATGA ARAAGGGCAG SCARCAGAGG KYRMA      35

(2) INFORMATION FOR SEQ ID NO:3:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:3:

GATCTTCGGC CACTTCTTCT GCAACGTCTT                                          30

(2) INFORMATION FOR SEQ ID NO:4:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: cDNA to mRNA (iii) HYPOTHETICAL: NO (iv) ANTI-SENSE: YES (xi) SEQUENCE DESCRIPTION: SEQ ID NO:4:

TGGGAACTTG TGTTTGGCTG CACTCTTCCT                                          30

(2) INFORMATION FOR SEQ ID NO:5:

(i) SEQUENCE CHARACTERISTICS:
    (A) LENGTH: 1505 base pairs
    (B) TYPE: nucleic acid
    (C) STRANDEDNESS: single
    (D) TOPOLOGY: linear (ii) MOLECULE TYPE: cDNA to mRNA (iii) HYPOTHETICAL: NO (iv) ANTI-SENSE: NO (vii) IMMEDIATE SOURCE:
    (B) CLONE: PCT-65 cDNA WITH INTRON (ix) FEATURE:
    (A) NAME/KEY: exon
    (B) LOCATION: 126..539

(ix) FEATURE:
    (A) NAME/KEY: intron
    (B) LOCATION: 540..611

(ix) FEATURE:
    (A) NAME/KEY: exon
    (B) LOCATION: 612..1409

(xi) SEQUENCE DESCRIPTION: SEQ ID NO:5:

CCTCCCCAGC GGCCGCCCCG ACCTCTCTAC GGCCATCTCC GTTCACTCAT CCTGCCGGAG          60

TGGGGCATGC TGGGCTGCAG GACCTGAGCC CGACGGTGGC ATGCCCACCT GTGGTGAGCT         120

CCTGGATGCC GCACCTGCTG AGTGGCTTCC TAGAGGTGAC GGCTAGCCCG GCGCCCACCT         180

GGGACGCGCC ACCGGACAAT GTCTCAGGCT GCGGGGAGCA GATCAACTAT GGCAGAGTGG         240

AGAAAGTTGT GATCGGCTCC ATCCTGACGC TCATCACGCT GCTGACGATC GCAGGCAACT         300

GCCTGGTGGT GATCTCGGTG TCCTTCGTCA AGAAGCTCCG CCAGCCCTCC AACTACCTGA         360

TTGTGTCCCT GGCCCTGGCT GACCTCTCGG TGGCCGTGGC GGTCATGCCT TTCGTTAGTG         420

```
TCACCGACCT CATCGGGGGC AAGTGGATCT TCGGCCACTT CTTCTGCAAC GTCTTCATCG      480

CCATGGACGT CATGTGCTGC ACGGCCTCGA TCATGACCCT GTGCGTGATC AGCATCGACA      540

GTCTGGCTTC GGTGTTTGAC CATGCTGTCG GTCTCCTGCT TACTGACTGG AGAGCCTTAC      600

TCTCGTCTTA AAGGTACCTT GGGATCACGA GACCCCTCAC GTACCCGGTG AGGCAAAATG      660

GGAAATGTAT GGCCAAAATG ATTCTGTCGG TCTGGCTGCT CTCTGCCTCC ATCACCTTAC      720

CTCCTCTCTT CGGATGGGCT CAGAATGTGA ACGATGACAA AGTGTGCTTG ATCAGCCAGG      780

ATTTTGGCTA CACGATCTAC TCCACTGCGG TGGCGTTTTA TATCCCCATG TCGGTCATGC      840

TGTTCATGTA CTATCAGATT TACAAGGCCG CCAGGAAGAG TGCAGCCAAA CACAAGTTCC      900

CAGGCTTCCC ACGCGTGCAG CCGGAGAGTG TCATCTCCCT GAATGGTGTG GTGAAGCTCC      960

AGAAGGAGGT GGAAGAGTGT GCGAACCTTT CGAGACTGCT CAAACACGAA AGGAAAAACA     1020

TCTCCATCTT CAAGCGGGAA CAGAAAGCAG CCACTACCTT GGGGATCATC GTGGGAGCCT     1080

TCACTGTGTG CTGGCTGCCG TTTTTCCTCT TGTCCACAGC CCGCCCCTTT ATCTGTGGCA     1140

CCTCCTGTAG CTGCATTCCT CTGTGGGTGG AGAGGACATG TCTGTGGCTG GGCTATGCAA     1200

ACTCTCTCAT TAATCCTTTT ATATATGCCT TCTTCAACCG GGACCTGAGG CCCACCTCTC     1260

GTAGCCTACT CCAGTGCCAG TACCGGAATA TCAACCGGAA GCTCTCTGCT GCAGGCATGC     1320

ATGAAGCCCT GAAACTTGCT GAGAGGCCCG AGAGATCCGA GTTTGTGCTA CAAAACTCTG     1380

ACCACTGTGG GAAAAAGGGT CATGATACAT GATCCAGAGT GGAACCCTGG ATGAATTCAT     1440

GCAGAACAGG TGGACACAAC ACAACGAATC ATTGGCTGAG ACTGCACATG GACATGCTCT     1500

GCTCT                                                                 1505

(2) INFORMATION FOR SEQ ID NO:6:

(i) SEQUENCE CHARACTERISTICS:
        (A) LENGTH: 1433 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (ix) FEATURE:
        (A) NAME/KEY: CDS
        (B) LOCATION: 126..1337

(xi) SEQUENCE DESCRIPTION: SEQ ID NO:6:

CCTCCCCAGC GGCCGCCCCG ACCTCTCTAC GGCCATCTCC GTTCACTCAT CCTGCCGGAG       60

TGGGGCATGC TGGGCTGCAG GACCTGAGCC CGACGGTGGC ATGCCCACCT GTGGTGAGCT      120

CCTGG ATG CCG CAC CTG CTG AGT GGC TTC CTA GAG GTG ACG GCT AGC          167
      Met Pro His Leu Leu Ser Gly Phe Leu Glu Val Thr Ala Ser
        1               5                  10

CCG GCG CCC ACC TGG GAC GCG CCA CCG GAC AAT GTC TCA GGC TGC GGG        215
Pro Ala Pro Thr Trp Asp Ala Pro Pro Asp Asn Val Ser Gly Cys Gly
 15                  20                  25                  30

GAG CAG ATC AAC TAT GGC AGA GTG GAG AAA GTT GTG ATC GGC TCC ATC        263
Glu Gln Ile Asn Tyr Gly Arg Val Glu Lys Val Val Ile Gly Ser Ile
                 35                  40                  45

CTG ACG CTC ATC ACG CTG CTG ACG ATC GCA GGC AAC TGC CTG GTG GTG        311
Leu Thr Leu Ile Thr Leu Leu Thr Ile Ala Gly Asn Cys Leu Val Val
             50                  55                  60
```

-continued

| | | |
|---|---|---|
| ATC TCG GTG TCC TTC GTC AAG AAG CTC CGC CAG CCC TCC AAC TAC CTG<br>Ile Ser Val Ser Phe Val Lys Lys Leu Arg Gln Pro Ser Asn Tyr Leu<br>           65                    70                  75 | 359 |
| ATT GTG TCC CTG GCC CTG GCT GAC CTC TCG GTG GCC GTG GCG GTC ATG<br>Ile Val Ser Leu Ala Leu Ala Asp Leu Ser Val Ala Val Ala Val Met<br>        80                   85                   90 | 407 |
| CCT TTC GTT AGT GTC ACC GAC CTC ATC GGG GGC AAG TGG ATC TTC GGC<br>Pro Phe Val Ser Val Thr Asp Leu Ile Gly Gly Lys Trp Ile Phe Gly<br>95                    100              105              110 | 455 |
| CAC TTC TTC TGC AAC GTC TTC ATC GCC ATG GAC GTC ATG TGC TGC ACG<br>His Phe Phe Cys Asn Val Phe Ile Ala Met Asp Val Met Cys Cys Thr<br>               115                   120              125 | 503 |
| GCC TCG ATC ATG ACC CTG TGC GTG ATC AGC ATC GAC AGG TAC CTT GGG<br>Ala Ser Ile Met Thr Leu Cys Val Ile Ser Ile Asp Arg Tyr Leu Gly<br>           130                  135              140 | 551 |
| ATC ACG AGA CCC CTC ACG TAC CCG GTG AGG CAA AAT GGG AAA TGT ATG<br>Ile Thr Arg Pro Leu Thr Tyr Pro Val Arg Gln Asn Gly Lys Cys Met<br>             145                  150              155 | 599 |
| GCC AAA ATG ATT CTG TCG GTC TGG CTG CTC TCT GCC TCC ATC ACC TTA<br>Ala Lys Met Ile Leu Ser Val Trp Leu Leu Ser Ala Ser Ile Thr Leu<br>160                   165              170 | 647 |
| CCT CCT CTC TTC GGA TGG GCT CAG AAT GTG AAC GAT GAC AAA GTG TGC<br>Pro Pro Leu Phe Gly Trp Ala Gln Asn Val Asn Asp Asp Lys Val Cys<br>175                   180              185              190 | 695 |
| TTG ATC AGC CAG GAT TTT GGC TAC ACG ATC TAC TCC ACT GCG GTG GCG<br>Leu Ile Ser Gln Asp Phe Gly Tyr Thr Ile Tyr Ser Thr Ala Val Ala<br>                    195              200              205 | 743 |
| TTT TAT ATC CCC ATG TCG GTC ATG CTG TTC ATG TAC TAT CAG ATT TAC<br>Phe Tyr Ile Pro Met Ser Val Met Leu Phe Met Tyr Tyr Gln Ile Tyr<br>             210                  215              220 | 791 |
| AAG GCC GCC AGG AAG AGT GCA GCC AAA CAC AAG TTC CCA GGC TTC CCA<br>Lys Ala Ala Arg Lys Ser Ala Ala Lys His Lys Phe Pro Gly Phe Pro<br>               225                 230              235 | 839 |
| CGC GTG CAG CCG GAG AGT GTC ATC TCC CTG AAT GGT GTG GTG AAG CTC<br>Arg Val Gln Pro Glu Ser Val Ile Ser Leu Asn Gly Val Val Lys Leu<br>           240                  245              250 | 887 |
| CAG AAG GAG GTG GAA GAG TGT GCG AAC CTT TCG AGA CTG CTC AAA CAC<br>Gln Lys Glu Val Glu Glu Cys Ala Asn Leu Ser Arg Leu Leu Lys His<br>255                   260              265              270 | 935 |
| GAA AGG AAA AAC ATC TCC ATC TTC AAG CGG GAA CAG AAA GCA GCC ACT<br>Glu Arg Lys Asn Ile Ser Ile Phe Lys Arg Glu Gln Lys Ala Ala Thr<br>                   275              280              285 | 983 |
| ACC TTG GGG ATC ATC GTG GGA GCC TTC ACT GTG TGC TGG CTG CCG TTT<br>Thr Leu Gly Ile Ile Val Gly Ala Phe Thr Val Cys Trp Leu Pro Phe<br>           290                  295              300 | 1031 |
| TTC CTC TTG TCC ACA GCC CGC CCC TTT ATC TGT GGC ACC TCC TGT AGC<br>Phe Leu Leu Ser Thr Ala Arg Pro Phe Ile Cys Gly Thr Ser Cys Ser<br>             305                  310              315 | 1079 |
| TGC ATT CCT CTG TGG GTG GAG AGG ACA TGT CTG TGG CTG GGC TAT GCA<br>Cys Ile Pro Leu Trp Val Glu Arg Thr Cys Leu Trp Leu Gly Tyr Ala<br>     320                   325              330 | 1127 |
| AAC TCT CTC ATT AAT CCT TTT ATA TAT GCC TTC TTC AAC CGG GAC CTG<br>Asn Ser Leu Ile Asn Pro Phe Ile Tyr Ala Phe Phe Asn Arg Asp Leu<br>335                   340              345              350 | 1175 |
| AGG CCC ACC TCT CGT AGC CTA CTC CAG TGC CAG TAC CGG AAT ATC AAC<br>Arg Pro Thr Ser Arg Ser Leu Leu Gln Cys Gln Tyr Arg Asn Ile Asn<br>                   355              360              365 | 1223 |
| CGG AAG CTC TCT GCT GCA GGC ATG CAT GAA GCC CTG AAA CTT GCT GAG<br>Arg Lys Leu Ser Ala Ala Gly Met His Glu Ala Leu Lys Leu Ala Glu<br>           370                  375              380 | 1271 |

```
AGG CCC GAG AGA TCC GAG TTT GTG CTA CAA AAC TCT GAC CAC TGT GGG          1319
Arg Pro Glu Arg Ser Glu Phe Val Leu Gln Asn Ser Asp His Cys Gly
        385                 390                 395

AAA AAG GGT CAT GAT ACA TGATCCAGAG TGGAACCCTG GATGAATTCA                 1367
Lys Lys Gly His Asp Thr
        400

TGCAGAACAG GTGGACACAA CACAACGAAT CATTGGCTGA GACTGCACAT GGACATGCTC        1427

TGCTCT                                                                   1433
```

(2) INFORMATION FOR SEQ ID NO:7:

(i) SEQUENCE CHARACTERISTICS:
        (A) LENGTH: 404 amino acids
        (B) TYPE: amino acid
        (D) TOPOLOGY: linear     (ii) MOLECULE TYPE: protein     (xi) SEQUENCE DESCRIPTION: SEQ ID NO:7:

```
Met Pro His Leu Leu Ser Gly Phe Leu Glu Val Thr Ala Ser Pro Ala
 1               5                  10                  15

Pro Thr Trp Asp Ala Pro Pro Asp Asn Val Ser Gly Cys Gly Glu Gln
            20                  25                  30

Ile Asn Tyr Gly Arg Val Glu Lys Val Val Ile Gly Ser Ile Leu Thr
        35                  40                  45

Leu Ile Thr Leu Leu Thr Ile Ala Gly Asn Cys Leu Val Val Ile Ser
    50                  55                  60

Val Ser Phe Val Lys Lys Leu Arg Gln Pro Ser Asn Tyr Leu Ile Val
 65                  70                  75                  80

Ser Leu Ala Leu Ala Asp Leu Ser Val Ala Val Ala Val Met Pro Phe
                85                  90                  95

Val Ser Val Thr Asp Leu Ile Gly Gly Lys Trp Ile Phe Gly His Phe
            100                 105                 110

Phe Cys Asn Val Phe Ile Ala Met Asp Val Met Cys Cys Thr Ala Ser
        115                 120                 125

Ile Met Thr Leu Cys Val Ile Ser Ile Asp Arg Tyr Leu Gly Ile Thr
    130                 135                 140

Arg Pro Leu Thr Tyr Pro Val Arg Gln Asn Gly Lys Cys Met Ala Lys
145                 150                 155                 160

Met Ile Leu Ser Val Trp Leu Leu Ser Ala Ser Ile Thr Leu Pro Pro
                165                 170                 175

Leu Phe Gly Trp Ala Gln Asn Val Asn Asp Asp Lys Val Cys Leu Ile
            180                 185                 190

Ser Gln Asp Phe Gly Tyr Thr Ile Tyr Ser Thr Ala Val Ala Phe Tyr
        195                 200                 205

Ile Pro Met Ser Val Met Leu Phe Met Tyr Tyr Gln Ile Tyr Lys Ala
    210                 215                 220

Ala Arg Lys Ser Ala Ala Lys His Lys Phe Pro Gly Phe Pro Arg Val
225                 230                 235                 240

Gln Pro Glu Ser Val Ile Ser Leu Asn Gly Val Val Lys Leu Gln Lys
                245                 250                 255

Glu Val Glu Glu Cys Ala Asn Leu Ser Arg Leu Leu Lys His Glu Arg
            260                 265                 270

Lys Asn Ile Ser Ile Phe Lys Arg Glu Gln Lys Ala Ala Thr Thr Leu
        275                 280                 285

Gly Ile Ile Val Gly Ala Phe Thr Val Cys Trp Leu Pro Phe Phe Leu
    290                 295                 300
```

```
Leu Ser Thr Ala Arg Pro Phe Ile Cys Gly Thr Ser Cys Ser Cys Ile
305                 310                 315                 320

Pro Leu Trp Val Glu Arg Thr Cys Leu Trp Leu Gly Tyr Ala Asn Ser
                325                 330                 335

Leu Ile Asn Pro Phe Ile Tyr Ala Phe Phe Asn Arg Asp Leu Arg Pro
                340                 345                 350

Thr Ser Arg Ser Leu Leu Gln Cys Gln Tyr Arg Asn Ile Asn Arg Lys
                355                 360                 365

Leu Ser Ala Ala Gly Met His Glu Ala Leu Lys Leu Ala Glu Arg Pro
370                 375                 380

Glu Arg Ser Glu Phe Val Leu Gln Asn Ser Asp His Cys Gly Lys Lys
385                 390                 395                 400

Gly His Asp Thr
```

(2) INFORMATION FOR SEQ ID NO:8:

(i) SEQUENCE CHARACTERISTICS:
        (A) LENGTH: 1417 base pairs
        (B) TYPE: nucleic acid
        (C) STRANDEDNESS: single
        (D) TOPOLOGY: linear     (ii) MOLECULE TYPE: cDNA     (iii) HYPOTHETICAL: NO     (iv) ANTI-SENSE: NO     (vii) IMMEDIATE SOURCE:
        (B) CLONE: Human PCT-65

(ix) FEATURE:
        (A) NAME/KEY: CDS
        (B) LOCATION: 8..1105

(xi) SEQUENCE DESCRIPTION: SEQ ID NO:8:

```
GAATTCC GGC GAG AAA GTT GTG ATC GGC TCC ATC CTG ACG CTC ATC ACG         49
        Gly Glu Lys Val Val Ile Gly Ser Ile Leu Thr Leu Ile Thr
        1               5                   10

CTG CTG ACG ATC GCG GGC AAC TGC CTG GTG GTG ATC TCC GTG TGC TTC         97
Leu Leu Thr Ile Ala Gly Asn Cys Leu Val Val Ile Ser Val Cys Phe
15              20                  25                  30

GTC AAG AAG CTC CGC CAG CCC TCC AAC TAC CTG ATC GTG TCC CTG GCG        145
Val Lys Lys Leu Arg Gln Pro Ser Asn Tyr Leu Ile Val Ser Leu Ala
                35                  40                  45

CTG GCC GAC CTC TCG GTG GCT GTG GCG GTC ATG CCC TTC GTC AGC GTC        193
Leu Ala Asp Leu Ser Val Ala Val Ala Val Met Pro Phe Val Ser Val
                50                  55                  60

ACC GAC CTC ATC GGG GGC AAG TGG ATC TTT GGA CAC TTT TTC TGT AAT        241
Thr Asp Leu Ile Gly Gly Lys Trp Ile Phe Gly His Phe Phe Cys Asn
                65                  70                  75

GTC TTC ATC GCC ATG GAC GTC ATG TGC TGC ACG GCC TCG ATC ATG ACC        289
Val Phe Ile Ala Met Asp Val Met Cys Cys Thr Ala Ser Ile Met Thr
80                  85                  90

CTG TGC GTG ATC AGC ATT GAC AGG TAC CTT GGG ATC ACA AGG CCC CTC        337
Leu Cys Val Ile Ser Ile Asp Arg Tyr Leu Gly Ile Thr Arg Pro Leu
95                  100                 105                 110

ACA TAC CCT GTG AGG CAG AAT GGG AAA TGC ATG GCG AAG ATG ATT CTC        385
Thr Tyr Pro Val Arg Gln Asn Gly Lys Cys Met Ala Lys Met Ile Leu
                115                 120                 125

TCC GTC TGG CTT CTC TCC GCC TCC ATC ACC TTA CCT CCA CTC TTT GGA        433
Ser Val Trp Leu Leu Ser Ala Ser Ile Thr Leu Pro Pro Leu Phe Gly
                130                 135                 140
```

```
TGG GCT CAG AAT GTA AAT GAT GAT AAG GTG TGC TTG ATC AGC CAG GAC        481
Trp Ala Gln Asn Val Asn Asp Asp Lys Val Cys Leu Ile Ser Gln Asp
            145                 150                 155

TTT GGC TAT ACG ATT TAC TCT ACC GCA GTG GCA TTT TAT ATC CCC ATG        529
Phe Gly Tyr Thr Ile Tyr Ser Thr Ala Val Ala Phe Tyr Ile Pro Met
        160                 165                 170

TCC GTC ATG CTT TTC ATG TAC TAC CAG ATT TAC AAG GCT GCC AGG AAG        577
Ser Val Met Leu Phe Met Tyr Tyr Gln Ile Tyr Lys Ala Ala Arg Lys
175                 180                 185                 190

AGT GCT GCC AAA CAC AAG TTT CCT GGC TTC CCT CGA GTG GAG CCA GAC        625
Ser Ala Ala Lys His Lys Phe Pro Gly Phe Pro Arg Val Glu Pro Asp
                195                 200                 205

AGC GTC ATC GCC CTG AAT GGC ATA GTG AAG CTC CAG AAG GAG GTG GAA        673
Ser Val Ile Ala Leu Asn Gly Ile Val Lys Leu Gln Lys Glu Val Glu
            210                 215                 220

GAG TGT GCA AAC CTT TCG AGA CTC CTC AAG CAT GAA AGG AAA AAC ATC        721
Glu Cys Ala Asn Leu Ser Arg Leu Leu Lys His Glu Arg Lys Asn Ile
        225                 230                 235

TCC ATC TTT AAG CGA GAA CAG AAA GCA GCC ACC ACC CTG GGG ATC ATC        769
Ser Ile Phe Lys Arg Glu Gln Lys Ala Ala Thr Thr Leu Gly Ile Ile
240                 245                 250

GTC GGG GCC TTT ACC GTG TGC TGG CTG CCA TTT TTC CTC CTC TCG ACA        817
Val Gly Ala Phe Thr Val Cys Trp Leu Pro Phe Phe Leu Leu Ser Thr
255                 260                 265                 270

GCC AGA CCC TTC ATC TGT GGC ACT TCC TGC AGC TGC ATC CCA CTG TGG        865
Ala Arg Pro Phe Ile Cys Gly Thr Ser Cys Ser Cys Ile Pro Leu Trp
                275                 280                 285

GTG GAG AGG ACA TTT CTG TGG CTA GGC TAT GCA AAC TCT CTC ATT AAC        913
Val Glu Arg Thr Phe Leu Trp Leu Gly Tyr Ala Asn Ser Leu Ile Asn
            290                 295                 300

CCT TTT ATA TAT GCC TTC TTC AAC CGG GAC CTG AGG ACC ACC TAT CGC        961
Pro Phe Ile Tyr Ala Phe Phe Asn Arg Asp Leu Arg Thr Thr Tyr Arg
        305                 310                 315

AGC CTG CTC CAG TGC CAG TAC CGG AAT ATC AAC CGG AAG CTC TCA GCT       1009
Ser Leu Leu Gln Cys Gln Tyr Arg Asn Ile Asn Arg Lys Leu Ser Ala
320                 325                 330

GCA GGC ATG CAT GAA GCC CTG AAG CTT GCT GAG AGG CCA GAG AGA CCT       1057
Ala Gly Met His Glu Ala Leu Lys Leu Ala Glu Arg Pro Glu Arg Pro
335                 340                 345                 350

GAG TTT GTG CTA CAA AAT GCT GAC TAC TGT AGA AAA AAA AGG TCA TGATTCAT1112
Glu Phe Val Leu Gln Asn Ala Asp Tyr Cys Arg Lys Lys Arg Ser
                355                 360                 365

TTGAAAGCAG AACAATGGAG ATGAAATAAA CAAGGCAAAA TAGAGGTGGA AACAGAAGGA     1172

AGTCATTTGC TGAGTCTGCA GAATGGAATG CAGCTTCTGT CCTTTCTTGG GATGTCTAAA    1232

ACATGACAAA CAGGGTGATC TGTTGTACAC ACTATCTTAT GAGGGAGATG GTGACTTCTC    1292

CTTTTTTCTG TGGATCAGTG CTATTGTGTG TTCTCAGTTT AAGATAGCAG ATCATCTCAG    1352

CAGTAAGCAC ACCAACAGAA CTGAGTTCCA GAAAGGAAGC AGTTTCTGGT GCTTTGCATA    1412

GATCC                                                                 1417
```

(2) INFORMATION FOR SEQ ID NO:9:

(i) SEQUENCE CHARACTERISTICS:
        (A) LENGTH: 365 amino acids
        (B) TYPE: amino acid
        (D) TOPOLOGY: linear     (ii) MOLECULE TYPE: protein     (xi) SEQUENCE DESCRIPTION: SEQ ID NO:9:

-continued

```
Gly Glu Lys Val Val Ile Gly Ser Ile Leu Thr Leu Ile Thr Leu Leu
 1               5                  10                 15

Thr Ile Ala Gly Asn Cys Leu Val Val Ile Ser Val Cys Phe Val Lys
            20                  25                  30

Lys Leu Arg Gln Pro Ser Asn Tyr Leu Ile Val Ser Leu Ala Leu Ala
            35                  40                  45

Asp Leu Ser Val Ala Val Ala Val Met Pro Phe Val Ser Val Thr Asp
     50                  55                  60

Leu Ile Gly Gly Lys Trp Ile Phe Gly His Phe Phe Cys Asn Val Phe
 65                  70                  75                  80

Ile Ala Met Asp Val Met Cys Cys Thr Ala Ser Ile Met Thr Leu Cys
                85                  90                  95

Val Ile Ser Ile Asp Arg Tyr Leu Gly Ile Thr Arg Pro Leu Thr Tyr
            100                 105                 110

Pro Val Arg Gln Asn Gly Lys Cys Met Ala Lys Met Ile Leu Ser Val
            115                 120                 125

Trp Leu Leu Ser Ala Ser Ile Thr Leu Pro Pro Leu Phe Gly Trp Ala
    130                 135                 140

Gln Asn Val Asn Asp Asp Lys Val Cys Leu Ile Ser Gln Asp Phe Gly
145                 150                 155                 160

Tyr Thr Ile Tyr Ser Thr Ala Val Ala Phe Tyr Ile Pro Met Ser Val
                165                 170                 175

Met Leu Phe Met Tyr Tyr Gln Ile Tyr Lys Ala Ala Arg Lys Ser Ala
            180                 185                 190

Ala Lys His Lys Phe Pro Gly Phe Pro Arg Val Glu Pro Asp Ser Val
            195                 200                 205

Ile Ala Leu Asn Gly Ile Val Lys Leu Gln Lys Glu Val Glu Glu Cys
    210                 215                 220

Ala Asn Leu Ser Arg Leu Leu Lys His Glu Arg Lys Asn Ile Ser Ile
225                 230                 235                 240

Phe Lys Arg Glu Gln Lys Ala Ala Thr Thr Leu Gly Ile Ile Val Gly
            245                 250                 255

Ala Phe Thr Val Cys Trp Leu Pro Phe Phe Leu Leu Ser Thr Ala Arg
            260                 265                 270

Pro Phe Ile Cys Gly Thr Ser Cys Ser Cys Ile Pro Leu Trp Val Glu
    275                 280                 285

Arg Thr Phe Leu Trp Leu Gly Tyr Ala Asn Ser Leu Ile Asn Pro Phe
    290                 295                 300

Ile Tyr Ala Phe Phe Asn Arg Asp Leu Arg Thr Thr Tyr Arg Ser Leu
305                 310                 315                 320

Leu Gln Cys Gln Tyr Arg Asn Ile Asn Arg Lys Leu Ser Ala Ala Gly
            325                 330                 335

Met His Glu Ala Leu Lys Leu Ala Glu Arg Pro Glu Arg Pro Glu Phe
            340                 345                 350

Val Leu Gln Asn Ala Asp Tyr Cys Arg Lys Lys Arg Ser
            355                 360                 365
```